US 9,770,542 B2

(12) United States Patent
Felber

(10) Patent No.: US 9,770,542 B2
(45) Date of Patent: Sep. 26, 2017

(54) DEVICE HAVING A FLOW CHANNEL, A NONRETURN VALVE, AND A FLOW DETECTOR THAT DETECTS A POSITION OF THE NONRETURN VALVE

(71) Applicant: MEDELA HOLDING AG, Baar (CH)

(72) Inventor: Armin Felber, Lucerne (CH)

(73) Assignee: MEDELA HOLDING AG, Baar (CH)

( * ) Notice: Subject to any disclaimer, the term of this patent is extended or adjusted under 35 U.S.C. 154(b) by 61 days.

(21) Appl. No.: 14/782,107

(22) PCT Filed: Mar. 27, 2014

(86) PCT No.: PCT/CH2014/000041
§ 371 (c)(1),
(2) Date: Oct. 2, 2015

(87) PCT Pub. No.: WO2014/161099
PCT Pub. Date: Oct. 9, 2014

(65) Prior Publication Data
US 2016/0038662 A1 Feb. 11, 2016

(30) Foreign Application Priority Data
Apr. 2, 2013 (CH) .................................. 698/13

(51) Int. Cl.
*A61M 1/00* (2006.01)
*F16K 37/00* (2006.01)
(Continued)

(52) U.S. Cl.
CPC .............. *A61M 1/06* (2013.01); *A61M 39/24* (2013.01); *F16K 15/031* (2013.01);
(Continued)

(58) Field of Classification Search
CPC ............ A61M 1/062; A61M 2039/244; A61M 2039/2446; A61M 2205/3334;
(Continued)

(56) References Cited

U.S. PATENT DOCUMENTS 3,857,277 A * 12/1974 Moore ....................... G01F 1/26
116/275
4,929,229 A * 5/1990 Larsson .................. A61M 1/06
119/14.25
(Continued)

FOREIGN PATENT DOCUMENTS

DE 3344196 A1 6/1985
DE 102008062532 A1 6/2009
(Continued)

OTHER PUBLICATIONS

English Translation of International Preliminary Report on Patentability for International Application No. PCT/CH2014/000041, issuance date Oct. 6, 2015.
(Continued)

*Primary Examiner* — Justin Olamit
(74) *Attorney, Agent, or Firm* — Marshall, Gerstein & Borun LLP

(57) ABSTRACT

A device having a flow channel for a fluid has a nonreturn valve arranged in the flow channel, the nonreturn valve allowing the fluid to flow through the flow channel in a first direction and preventing it from flowing through the flow channel in a direction counter to the first direction. The device furthermore has a flow detector for detecting the flow of the fluid through the flow channel, wherein the flow detector detects a change in the nonreturn valve. This detected change serves as an indicator for the flow of the fluid. The device enables simplified flow detection, in that a nonreturn valve that is present is used as an indicator.

14 Claims, 2 Drawing Sheets

(51) Int. Cl.
*A61M 1/06* (2006.01)
*A61M 39/24* (2006.01)
*F16K 15/03* (2006.01)
*G01F 22/00* (2006.01)
*F16K 15/14* (2006.01)

(52) U.S. Cl.
CPC .......... *F16K 37/0058* (2013.01); *G01F 22/00* (2013.01); *A61M 2039/244* (2013.01); *A61M 2039/246* (2013.01); *A61M 2205/3334* (2013.01); *F16K 15/144* (2013.01); *F16K 37/0075* (2013.01); *F16K 37/0091* (2013.01)

(58) Field of Classification Search
CPC .... A61M 2039/246; A61M 2039/2433; A61M 2039/242; A61M 39/24; A61M 1/06; F16K 37/0058; F16K 37/0075; F16K 37/0083; F16K 37/0091
See application file for complete search history.

(56) References Cited

U.S. PATENT DOCUMENTS

| | | | |
|---|---|---|---|
| 4,964,851 A | 10/1990 | Larsson | |
| 6,257,847 B1 | 7/2001 | Silver et al. | |
| 6,457,354 B1 * | 10/2002 | Huang | H03K 17/968 137/554 |
| 6,497,677 B2 | 12/2002 | Silver | |
| 6,547,756 B1 | 4/2003 | Greter et al. | |
| 6,673,036 B1 | 1/2004 | Britto | |
| 8,070,716 B2 | 12/2011 | Sutrina et al. | |
| 8,608,685 B2 | 12/2013 | Tashiro et al. | |
| 2011/0301532 A1 | 12/2011 | Wach et al. | |
| 2012/0022451 A1 | 1/2012 | Silver | |
| 2013/0096461 A1 * | 4/2013 | Sella | A61M 1/06 600/573 |

FOREIGN PATENT DOCUMENTS

| | | |
|---|---|---|
| EP | 1430918 A1 | 6/2004 |
| WO | WO-9836245 A1 | 8/1998 |
| WO | WO-2007/085100 A2 | 8/2007 |
| WO | WO-2008/141471 A1 | 11/2008 |
| WO | WO-2013/049944 A1 | 4/2013 |

OTHER PUBLICATIONS

International Search Report for Application No. PCT/CH2014/000004, mailed May 20, 2014.

* cited by examiner

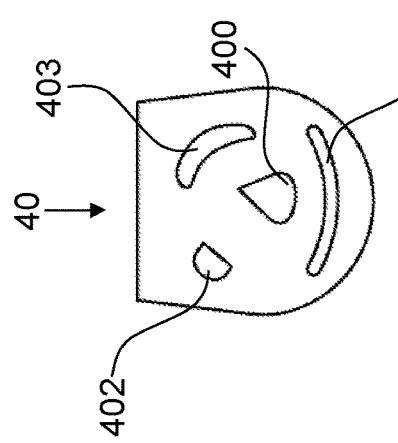
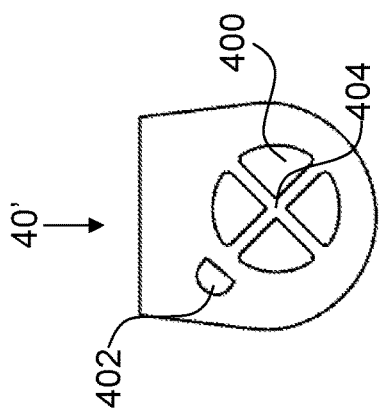
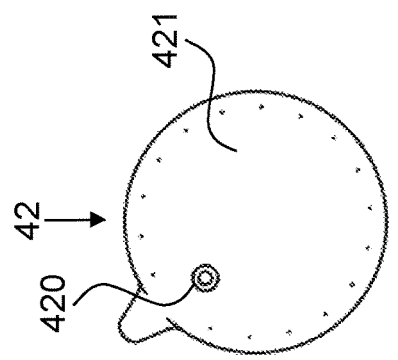
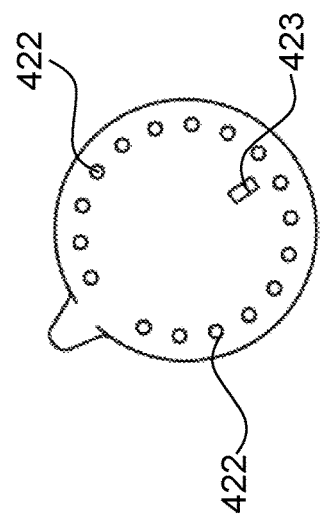
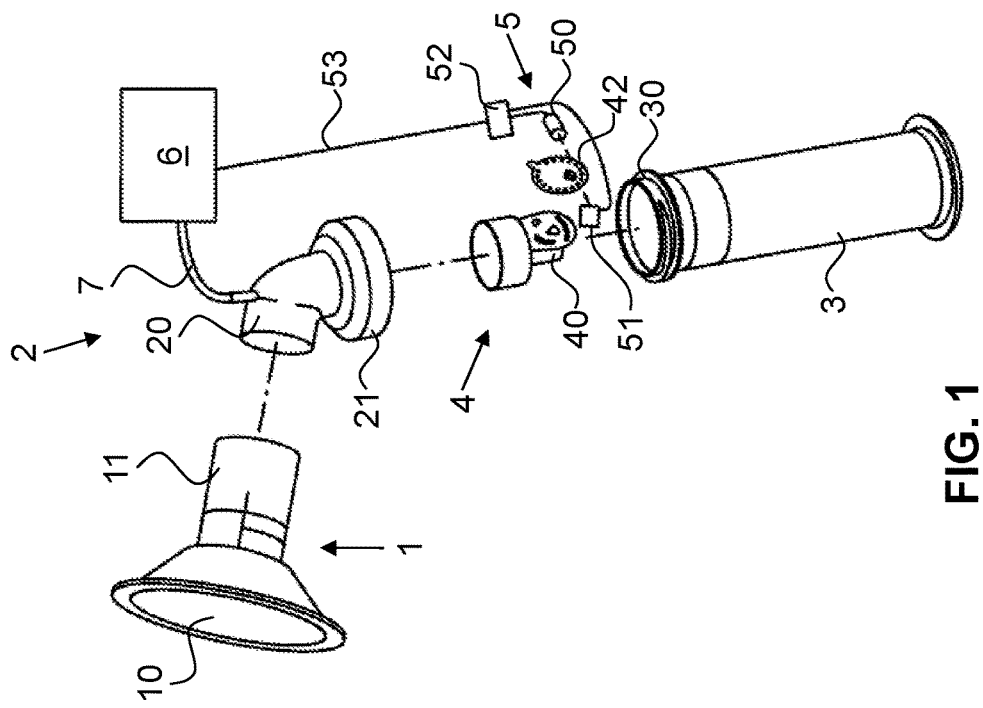

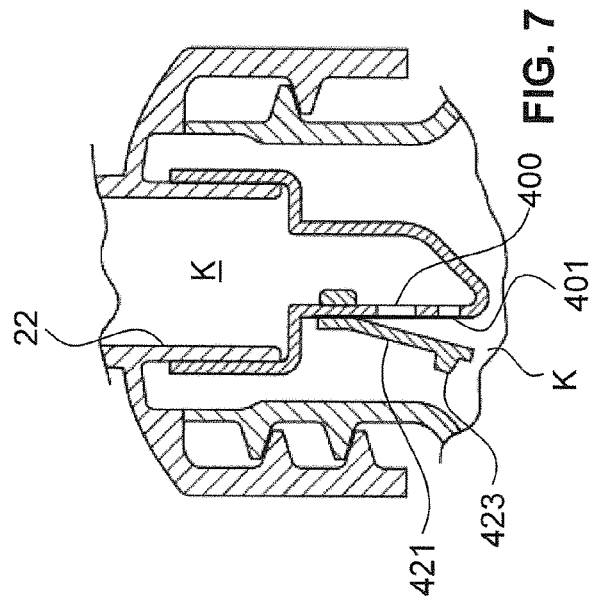
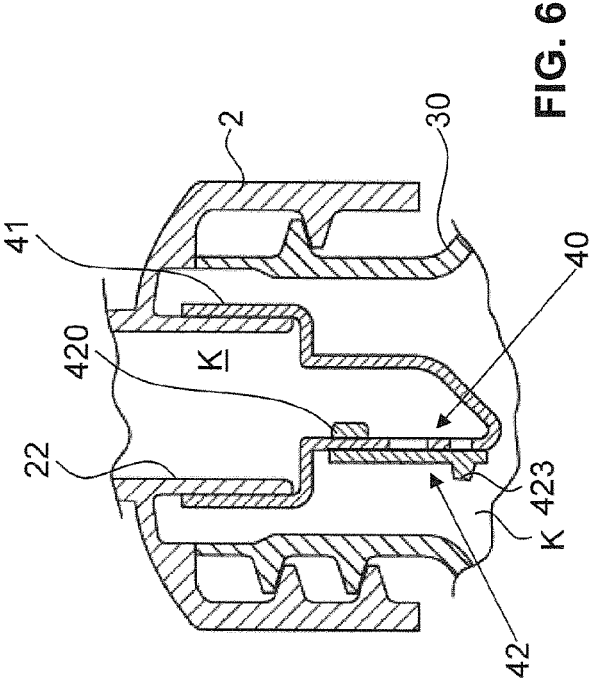
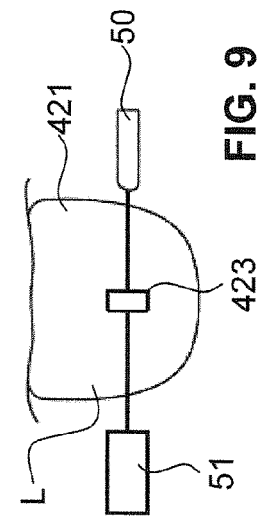
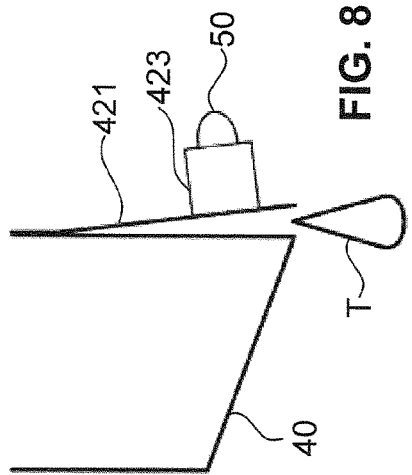

DEVICE HAVING A FLOW CHANNEL, A NONRETURN VALVE, AND A FLOW DETECTOR THAT DETECTS A POSITION OF THE NONRETURN VALVE

CROSS-REFERENCE TO RELATED APPLICATION

The present application is the US national phase of International Patent Application No. PCT/CH2014/000041, filed Mar. 27, 2014, which application claims priority to Switzerland patent application CH 0698/13, filed Apr. 2, 2013. The priority application, CH 0698/13, is hereby incorporated by reference.

TECHNICAL FIELD OF THE DISCLOSURE

The present invention relates to a device having a flow channel. In a preferred application field, this device is a breast shield of a breastpump unit for expressing human breast milk or an adapter between the breast shield and a milk collection container.

PRIOR ART

In order to express human breast milk, motor-driven or manually operated breastpump units are used. This breastpump unit has one or two breast shields which are placed on the breast and surround the nipple. By means of a vacuum pump, a negative pressure is applied in the breast shield, said negative pressure preferably varying cyclically. A breastmilk bottle is screwed directly or via an adapter onto the breast shield in order that expressed milk can flow directly into a collecting container. Such breastpump units are well known, for example from U.S. Pat. Nos. 6,497,677, 4,964,851, 6,547,756 and 6,257,847.

In order to limit the dead volume in the breast shield, the breast shield or the adapter has a nonreturn valve which opens a passage to the interior of the breastmilk bottle. The nonreturn valve is for example a diaphragm valve having a valve diaphragm, as is disclosed in some of the abovementioned patent publications and also in U.S. Pat. Nos. 4,929,229, 8,070,716 and 2011/0301532.

EP 1 430 918 describes a system for detecting the milk surge. For this purpose, a milk collection container is placed on a balance during expression, in order to determine the amount of milk expressed as a function of time.

Furthermore, international patent application PCT/CH2012/000222 discloses a vacuum pump for use in a breastpump unit which has a media separating diaphragm. This diaphragm also serves as a sensor diaphragm for determining the negative pressure generated. For this purpose, the diaphragm has a protruding lug, the position of which is detected optically.

US 2012/0022451 discloses a pump unit for an enteral feeding device. This pump unit has a double chamber separated by a diaphragm. The diaphragm is provided in one embodiment with an indicator rod which rises and drops in a manner corresponding to the movement of the diaphragm and serves as a measure of the fluid located in a chamber.

SUMMARY OF THE INVENTION

It is an object of the invention to already obtain an indication for a fluid flow during the expressing operation, preferably as a measure of the amount of fluid expressed.

The device according to the invention has a flow channel for a fluid. A nonreturn valve is arranged in the flow channel, said nonreturn valve allowing the fluid to flow through the flow channel in a first direction and preventing it from flowing through the flow channel in a direction counter to the first direction. The device furthermore has a flow detector for detecting the flow of the fluid through the flow channel, wherein the flow detector detects a change in the nonreturn valve. This detected change serves as an indicator for the flow.

Preferably, the flow detector is a flow meter for determining the flow, wherein the detected change serves as a measure of the flow.

In preferred exemplary embodiments, the device is part of a breast shield or of an adapter between the breast shield and a milk collection container. In this case, the fluid is the expressed milk. The fluid collection container is the breastmilk container.

However, the device according to the invention can also be used in other fields, for example in drainage devices, in particular for thoracic drainage or wound drainage. The fluid can in this case be an aspirated secretion or air. In these application fields, the device is arranged preferably in the region of a fluid collection container. For example, a cover of a fluid collection container according to WO 2008/141471 or WO 2007/085100 can be equipped with such a nonreturn valve and flow detector.

When a fluid flows through the valve, the latter opens and as a result its shape or position in the space changes. This is thus a detectable indicator for the fluid flow.

If a large amount of fluid flows through the valve, i.e. if the flow volume is high, then the change of the nonreturn valve relative to its rest position without any flow is greater than when the flow volume is low. In other words, the nonreturn valve has to open more in the case of a larger amount of fluid than in the case of a smaller amount. As a result, a measure of the flow can be obtained easily.

This measure can be indicated, for example, with or without further calculations, graphically on a display, so that for example the mother can easily recognize whether the amount of milk expressed is increasing or decreasing or whether it is remaining constant. The same also applies for other application fields.

This measure can also be evaluated by means of an electronic evaluation unit. For example the flow rate, i.e. the flow volume per unit time, can be calculated. Furthermore, the flow volume or the entire amount of milk expressed can be calculated. Likewise, the time of the milk surge, i.e. the time at which the milk begins to flow at a maximum, can be determined. The same also applies for other application fields.

The flow detector can detect the change in the nonreturn valve in different ways, for example optically or mechanically. Preferably, the flow detector has an optical detector for detecting the change in the nonreturn valve. In a preferred embodiment, the optical detector comprises a light emitter and a light detector, wherein the nonreturn valve is arranged, in the changed and/or in the unchanged state, in a light path between the light emitter and the light detector. Preferably, the nonreturn valve is arranged such that it interrupts the light path at least in the changed state.

The position of the nonreturn valve can be detected easily when the nonreturn valve has a valve diaphragm, wherein the flow detector detects a deflection of the valve diaphragm. Detection is made easier when the valve diaphragm has a valve flap. If little fluid flows, the diaphragm flap is scarcely deflected, and at a larger flow volume, it moves further away from the valve opening of its valve seat. The larger the valve diaphragm, the greater the travel. This increases the accuracy of the measurement. The travel can also be increased in that the valve flap is fastened to the valve seat in a first peripheral region and is movable relative to the valve seat in a second peripheral region located opposite the first peripheral region; i.e. the valve flap is fastened off-centre on one side.

Preferably, the nonreturn valve, in particular the valve diaphragm, is provided with a fin or rigid lug, the position of which is detected by the flow detector. This also makes detection easier, and additionally has the advantage that the mode of operation of the nonreturn valve is not impaired. Preferably, the lug is arranged on the valve diaphragm, in particular in a manner protruding perpendicularly from a main surface of the valve diaphragm. In this case, the lug is arranged preferably in the light path. In the case of a valve flap fastened on one side, the lug is arranged preferably in the peripheral region located opposite the fastening, in order to cover a travel which is as large as possible during the movement of the diaphragm.

Preferably, the valve diaphragm is formed in a planar manner, wherein said valve diaphragm is provided preferably on its planar main surface with knobs which are arranged on the top side, facing away from the valve seat, of the main surface.

Further embodiments are given in the dependent claims.

BRIEF DESCRIPTION OF THE DRAWINGS

Preferred embodiments of the invention are described in the following text with reference to the drawings, which serve merely for illustration and are not to be interpreted in a limiting manner. In the drawings:

FIG. 1 shows a partial perspective illustration of a breastpump unit having a device according to the invention;

FIG. 2 shows a view from the rear of a valve diaphragm of the device according to FIG. 1;

FIG. 3 shows a view from the front of a valve seat of the device according to FIG. 1, in a mirror image;

FIG. 4 shows a view from the front of the valve diaphragm according to FIG. 2;

FIG. 5 shows a second embodiment of a valve seat of the device;

FIG. 6 shows a longitudinal section through a part of the breastpump unit having the device according to the invention in a third exemplary embodiment with the nonreturn valve closed;

FIG. 7 shows a longitudinal section through the part of the breastpump unit according to FIG. 6 with the nonreturn valve open;

FIG. 8 shows a schematic illustration of the device according to the invention in a side view; and FIG. 9 shows a view from the front of the illustration according to FIG. 8.

DETAILED DESCRIPTION OF PREFERRED EMBODIMENTS

FIG. 1 illustrates a breastpump unit for expressing human breast milk. It has a breast shield 1 for placing in a sealing manner against the human breast, a milk collection container 3 for collecting the expressed breast milk and an adapter 2 for detachably connecting the breast shield 1 to the milk collection container 3. The adapter 2 and the breast shield 1 can be formed as separate parts or together in one piece.

The breast shield 1 may have a form that is known from the prior art. What is illustrated is a conventional form having a funnel 10 for placing on the breast and a connection piece 11 integrally formed thereon for connecting to the adapter 2. The adapter 2 usually has a connection piece 20 for receiving the connection piece 11 of the breast shield 1 and also, at an angle thereto, a threaded part 21 for connecting to a neck 30 of the milk collection container. The milk collection container may be formed in a rigid form, for example as a plastics bottle, or in a flexible form, for example as a milk bag.

The breastpump unit furthermore comprises a vacuum pump 6 which is connected via a suction line to the adapter 2 or the breast shield 1. The vacuum pump 6 may be a pump that is driven by an electric motor or may be a manually operated pump. It may be arranged on the breast shield 1 or on the adapter 2 such that the breastpump unit is in the form of a portable breastpump. However, it may also be a separate unit from the adapter 2. Examples of all variants have already been mentioned at the beginning.

By means of the vacuum pump 6, a, preferably cyclically varying, negative pressure is applied in the breast shield 1 and in this way the breast milk is expressed. In order to limit the dead volume, a nonreturn valve 4 is present in a known manner. In this example, it is arranged on the adapter part 2. The nonreturn valve 4 has a valve seat 40 having at least one flow opening 400, 401, 403, which is closed by a valve diaphragm 42. The valve diaphragm 42 is manufactured preferably from a flexible plastics material, in particular silicone.

In this example, the valve seat 40 has a collar 41 which is plugged onto a corresponding inner tube section 22 which is illustrated in FIGS. 6 and 7. However, the valve seat 40 may also be integrally formed in the adapter part 2 or in the breast shield 1.

The flow openings 400, 401, 403 may be formed in various ways. They may be separated from one another for example by crosspieces 404. FIGS. 3 and 5 show two possible examples.

The valve diaphragm 42 is formed preferably in one piece. It has preferably an approximately circular or oval shape. However, other shapes are likewise possible. Its main body 421 is preferably formed in a flat and relatively thin manner. The approximately planar rear side of the main body 421, i.e. the side facing the valve seat, is illustrated in FIG. 2. On this rear side, the valve diaphragm has a knob 420 which is pluggable into a corresponding fastening opening 402 in the valve seat 40. This knob 420 may be arranged centrally on the main body 421. However, it is preferably located in a peripheral region such that the valve diaphragm forms a valve flap. The front side of the valve diaphragm, which is illustrated in FIG. 4, may be formed in a planar manner or it may have, as illustrated here, a plurality of protruding reinforcement knobs 422.

According to the invention, the breastpump unit furthermore has a flow detector 5, preferably a flow meter. This flow detector 5 detects or measures a change in the nonreturn valve 4 when a fluid, in this case milk, flows through the nonreturn valve 4. The flow detector 5 is in this case for example an optical detection unit, which comprises a light emitter 50, for example a light emitting diode or a light emitting diode array, and a light detector 51, for example a photodiode or photodiode array.

The valve diaphragm 42 has a nose or lug 423 protruding from the front side, as can be seen in FIG. 4. It protrudes preferably perpendicularly to the surface of the main body 421. This lug 423 projects, as is illustrated in FIG. 9, into a light path L which is formed by the light emitter 50 and light detector 51. An evaluation unit 52, see FIG. 1, is connected to the light emitter 50 and the light detector 51. It may be arranged for example in the region of the light detector 51 or it may be integrated in the housing of the vacuum pump 6. The signal from the light detector 51 or the result from the evaluation unit 52 are passed via a connecting line 53 to the vacuum pump 6. The signal or the data may also be transmitted wirelessly.

FIG. 6 illustrates the valve diaphragm 4 when no milk is flowing. The flow channel K, formed by the interior of the breast shield 1 or of the adapter 2 and the interior of the milk collection container 3, is interrupted by the nonreturn valve 4.

If a fluid, in this case a drop of milk T, now flows through this flow channel K, the valve 4 opens, as is illustrated in FIGS. 7 and 8. The valve diaphragm 42 is pivoted about the fastening knob 420 and the lug 423 is deflected. This deflection is detected by the optical flow detector 5.

The detection can take place in various ways. A simple deflection may be detected. For example, the lug 423 is located outside the light path L in the non-deflected state, and all that is detected is that the lug 423 has moved. Thus, all that is detected is that a fluid is now flowing; however, no conclusions are drawn about the quantity. This result can be represented optically, acoustically or in some other way on the breastpump unit.

However, the degree of deflection may also be determined, in that the extent to which the lug 423 projects into the light path is detected. The extent of the deflection provides information about the amount of fluid that has flowed through the valve. Since the vacuum is usually applied cyclically to the breast, the milk also does not flow uniformly. The amount of milk per individual stroke and the amount of milk over a predetermined period of time can be determined. Both can be represented optically, for example graphically and quantitatively, on a display of the breastpump unit. It has been shown that in the case of use with a breast shield, the valve can already slightly open during the application of the negative pressure to the breast shield, without milk already flowing. This opening usually takes place cyclically, analogously to the rise in pressure in the breast shield. However, this additional deflection can be taken into account during the evaluation of the signal and does not as a result falsify the result.

As already mentioned, the same principle of flow detection and flow measurement can also be used in other fields, for example in the case of a drainage device.

The device according to the invention enables flow detection with simple means, in that a nonreturn valve that is present is used as an indicator means.

The invention claimed is:

1. A device having a flow channel for a fluid, wherein a nonreturn valve is arranged in the flow channel, said nonreturn valve allowing the fluid to flow through the flow channel in a first direction and preventing it from flowing through the flow channel in a direction counter to the first direction, wherein the device furthermore has a flow detector for detecting the flow of the fluid through the flow channel, wherein the flow detector detects a change in the nonreturn valve and wherein this detected change serves as an indicator for the flow of the fluid, wherein the nonreturn valve has a valve flap, wherein the flow detector has an optical or mechanical detector for detecting a deflection of the valve flap, wherein the valve flap opens and closes a valve seat of the nonreturn valve, wherein the valve flap is fastened to the valve seat in a first peripheral region and is movable relative to the valve seat in a second peripheral region located opposite the first peripheral region, wherein the nonreturn valve is provided with a lug arranged on the valve flap, wherein a position of the lug is detected by the flow detector.

2. The device according to claim 1, wherein the flow detector is a flow meter for determining the flow and wherein the detected change serves as a measure of the flow.

3. The device according to claim 1, wherein the optical detector comprises a light emitter and a light detector, wherein the nonreturn valve is arranged, in the changed and/or in the unchanged state, in a light path between the light emitter and the light detector.

4. The device according to claim 3, wherein the lug is arranged in the light path.

5. The device according to claim 1, wherein the lug is arranged in the second peripheral region.

6. The device according to claim 1, wherein the device is a breast shield of a breastpump unit for expressing human breast milk, wherein the breast shield is designed to be placed on a human breast.

7. The device according to claim 1, wherein the device is an adapter for connecting to a fluid collection container.

8. The device according to claim 1, wherein the device is part of a drainage device.

9. The device of claim 8, wherein the drainage device is part of a fluid collection container.

10. A breastpump system comprising:
a device according to claim 1 connectable to at least one of a breastshield and a fluid channel between the breastshield and a collection container of the system, the system comprising a display configured to represent information about the amount of milk flowing in the system.

11. The breastpump system as claimed in claim 10, the device determining the deflection of the nonreturn valve, the display connectable, directly or indirectly, to the breastpump system.

12. A method for detecting flow of fluid through a flow channel, wherein a nonreturn valve is arranged in the flow channel, wherein the nonreturn valve allows fluid to flow through the flow channel in a first direction and prevents fluid from flowing through the flow channel in a direction counter to the first direction, wherein the nonreturn valve has a valve flap, wherein the valve flap opens and closes a valve seat of the nonreturn valve, wherein the valve flap is fastened to the valve seat in a first peripheral region and is movable relative to the valve seat in a second peripheral region located opposite the first peripheral region and wherein the nonreturn valve is provided with a lug arranged on the valve flap, the method comprising the step of:
detecting, via a flow detector, a change in at least one of position or shape of a nonreturn valve arranged when a fluid flows through the nonreturn valve, the flow detector having an optical or mechanical detector detecting a deflection of the valve flap, wherein the optical or mechanical detector detects a position of the lug.

13. The method of claim 12, detecting the change in at least one of position or shape of the nonreturn valve, detecting a degree of deflection of the nonreturn valve, and based on the detected degree of deflection of the nonreturn valve, calculating a volume of fluid that has flowed through the nonreturn valve.

14. The method according to claim 13, further comprising repeatedly detecting the degree of deflection of the nonreturn valve for a plurality of deflections of the nonreturn valve over a predetermined period of time, and adding the calculated volumes of fluid that have flowed through the nonreturn valve to determine a volume of fluid that has flowed through the nonreturn valve over the predetermined period of time.

* * * * *